United States Patent
Hartwich et al.

(10) Patent No.: US 8,480,303 B2
(45) Date of Patent: Jul. 9, 2013

(54) MOVEMENT CONTROL FOR A MOBILE X-RAY SYSTEM

(75) Inventors: Reinhold Hartwich, Pleystein (DE); Norbert Herrmann, Ebnath (DE); Josef Rupprecht, Erbendorf (DE); Manfred Sechser, Neusorg (DE)

(73) Assignee: Siemens Aktiengesellschaft, München (DE)

( * ) Notice: Subject to any disclaimer, the term of this patent is extended or adjusted under 35 U.S.C. 154(b) by 199 days.

(21) Appl. No.: 12/874,908

(22) Filed: Sep. 2, 2010

(65) Prior Publication Data
US 2011/0058656 A1    Mar. 10, 2011

(30) Foreign Application Priority Data
Sep. 8, 2009    (DE) .......................... 10 2009 040 611

(51) Int. Cl.
*H05G 1/02*    (2006.01)
*H05G 1/00*    (2006.01)

(52) U.S. Cl.
USPC .......................................... 378/198; 378/193

(58) Field of Classification Search
USPC ................. 378/198, 193, 194, 196, 197, 204, 378/210
See application file for complete search history.

(56) References Cited

U.S. PATENT DOCUMENTS

| | | | | |
|---|---|---|---|---|
| 3,790,805 | A  * | 2/1974 | Foderaro | 378/198 |
| 4,326,131 | A  * | 4/1982 | Waerve | 378/198 |
| 7,016,467 | B2 * | 3/2006 | Brooks | 378/102 |
| 2004/0146142 | A1* | 7/2004 | Maijala | 378/102 |
| 2008/0118036 | A1 | 5/2008 | Jensen et al. | |
| 2010/0329426 | A1* | 12/2010 | Oda et al. | 378/98.2 |
| 2010/0329427 | A1* | 12/2010 | Takae et al. | 378/98.5 |

FOREIGN PATENT DOCUMENTS

| | | |
|---|---|---|
| DE | 19631246 A1 | 2/1998 |
| DE | 10084738 T1 | 1/2001 |
| DE | 10111800 A1 | 10/2002 |
| DE | 102006046689 A1 | 4/2008 |
| WO | WO 01/01860 A1 | 11/2001 |

OTHER PUBLICATIONS

German Office Action dated May 18, 2010 for corresponding German Patent Application No. DE 10 2009 040 611.5 with English translation.

* cited by examiner

*Primary Examiner* — Anastasia Midkiff
(74) *Attorney, Agent, or Firm* — Lempia Summerfield Katz LLC

(57) ABSTRACT

A mobile x-ray device that is operable to be moved for a change in position and is operable to be controlled and braked during movement is provided. A handle is arranged on the x-ray device, and the handle is operable to both control and brake the mobile x-ray device. The combination of control and braking in a handle results in improved manageability and allows for a more compact design.

15 Claims, 3 Drawing Sheets

MOVEMENT CONTROL FOR A MOBILE X-RAY SYSTEM

This application claims the benefit of DE 10 2009 040 611.5 filed Sep. 8, 2009, which is hereby incorporated by reference.

BACKGROUND

The present embodiments relate to a mobile x-ray device.

X-ray devices relate to a wide spread of diagnostic devices within medical technology. It may not be desirable to have a purely stationary x-ray device. Instead a spatial moveability of the x-ray device may be provided. The mobile x-ray device can be used at various treatment positions and can thus be combined with various modalities, for example, or positioned in accordance with the optimal use of the space available in the hospital.

One example of moveable x-ray systems are ceiling systems, in which the x-ray device may be moved along by rails. X-ray devices that are provided with wheels and can be moved across the hospital floor exhibit an even greater degree of flexibility. An x-ray system of this type is disclosed in DE 10 2006 046 689 A1, for example.

In the case of x-ray devices provided with wheels, a moveability that is easy to handle must be provided in practice. For example, the device is able to be steered and/or controlled and braked. Attention may also be paid to the device being as easily controllable as possible when moved and to the facilities needed for the control allowing for a compact design of the device in order to keep the size of the device as minimal as possible.

SUMMARY AND DESCRIPTION

The present embodiments may obviate one or more of the drawbacks or limitations in the related art. For example, in one embodiment, a mobile x-ray device may be controlled when moved.

In accordance with the present embodiments, a handle is provided on the x-ray device. The handle is suited for controlling and/or steering and also braking the x-ray device. The handle is a multifunctional handle and/or combined brake and steering handle.

The steering process may be carried out by rotating the handle and the braking by exerting pressure on the handle. The pressure exerted for braking is exerted in a different direction than a pressure exerted for rotating the handle. The pressure exerted for braking may include, for example, a depression or lifting of the handle relative to the device. In one embodiment, the pressure exerted for braking may include retraction or forward depression.

The present embodiments are advantageous in that two functions are realized in one handle. This results in improved manageability of the x-ray device, since the hospital personnel do not have to actuate the steering and/or braking action at two different points. This also results in a more compact design of the x-ray device, since only one apparatus element (multifunctional handle) is needed for two separate functions.

In one embodiment, a display is provided on the handle. The display provides information relating to the braking state (e.g. whether the handle is in a braking position). The operating personnel are able to control whether a deblocking of the wheels to allow movement of the wheels is carried out. Braking and steering may be realized within the x-ray device using Bowden cable elements, which are controlled by the handle relative to the wheels and/or wheel control elements.

This is advantageous with respect to a compact design of the x-ray device, since the Bowden cable elements are flexible and space-saving when laid in the x-ray device.

DETAILED DESCRIPTION OF THE DRAWINGS

Figure 1:
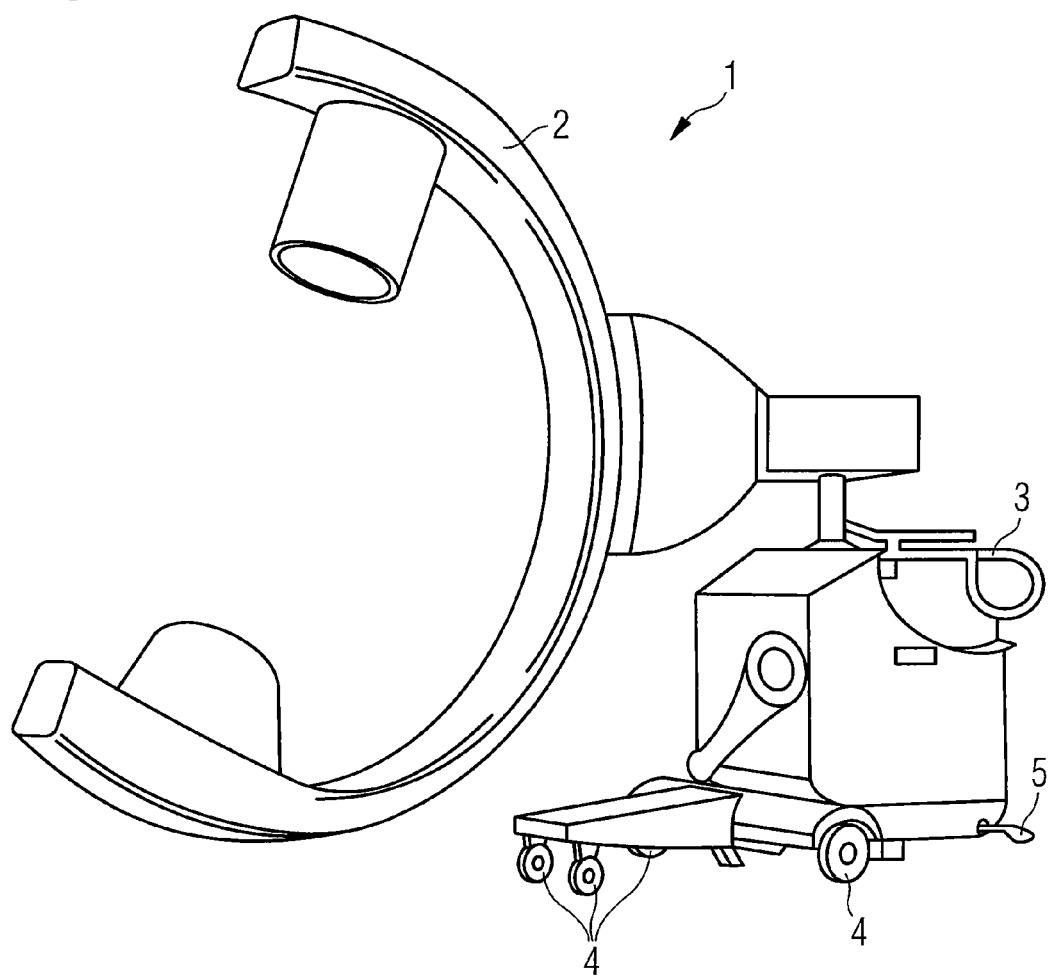
FIG. 1 shows a conventional mobile x-ray device.

FIG. 1 shows a mobile x-ray device 1 (e.g., a mobile C-arm 1). The mobile C-arm 1 includes an arc 2 including an x-ray source and an x-ray detector. The arc 2 is fastened to a stand 3. The stand 3 includes wheels 4, which are used to move the mobile C-arm across the floor. The mobile C-arm 1 also includes a brake element and/or a foot break 5 that enables a braking using foot pressure.

Figure 2:
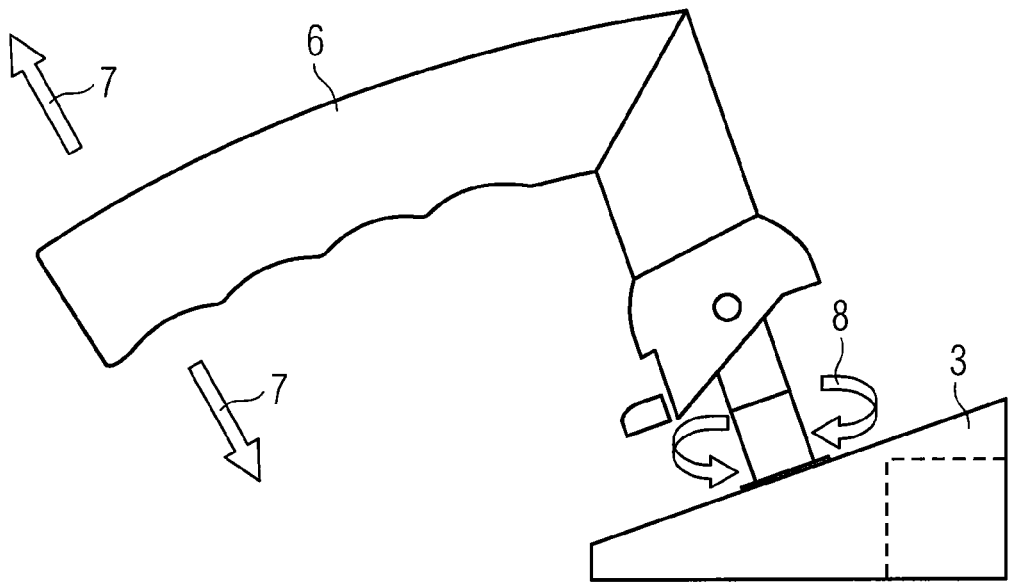
FIG. 2 shows one embodiment of a handle.
Figure 3:
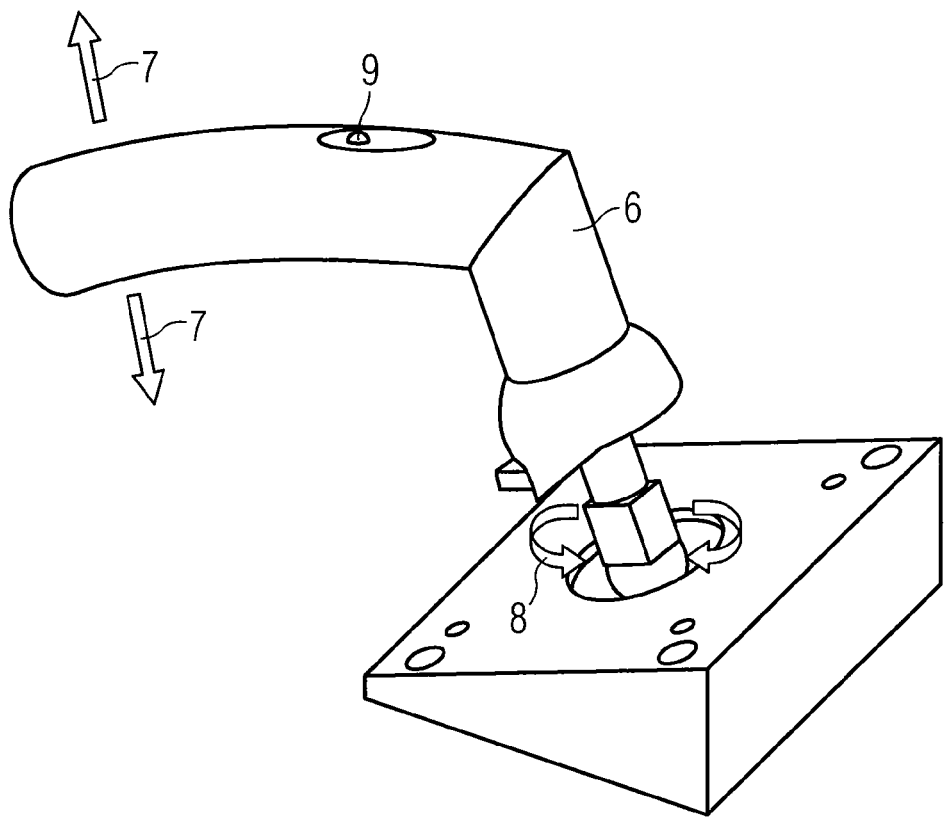
FIG. 3 shows one embodiment of a handle with status displays for the braking status.

In accordance with the present embodiments, the braking function and steering function are combined by a handle provided for both functions. A multifunctional handle 6 of this type is shown in FIG. 2. By lifting or depressing 7 the handle 6, a brake in the mobile C-arm device is actuated. For control, the handle 6 may be rotated 8. The rotation activates the steering of the C-arm system. In one embodiment, the handle 6 includes an integrated status indicator 9 for the braking status (as shown in FIG. 3). The status indicator 9 allows operating personnel to see whether the handle 6 is in a brake position, which blocks the wheels. The status indicator 9 may be realized mechanically and/or electronically.

Figure 4:
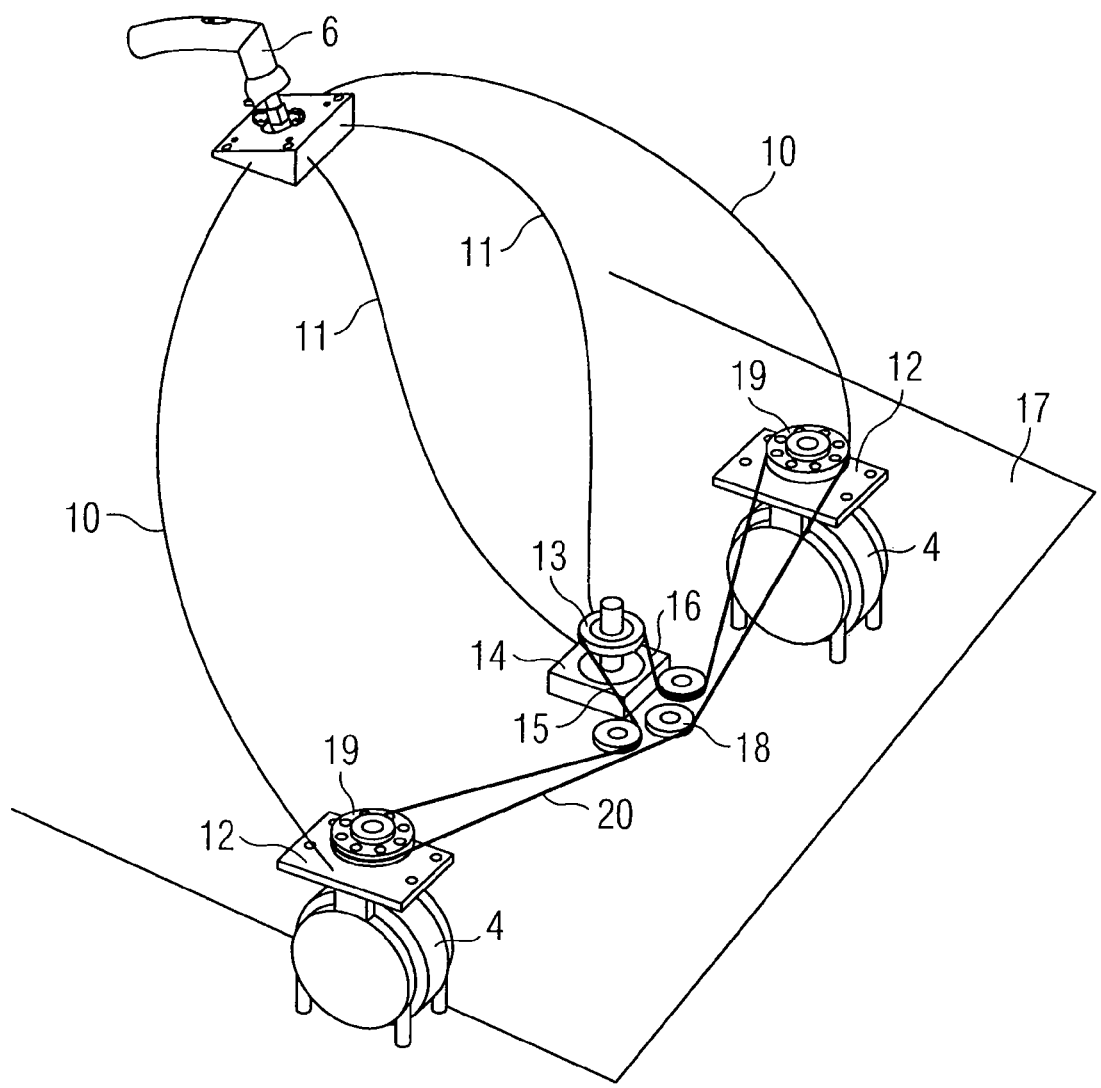
FIG. 4 shows steering and braking functions of one embodiment of the handle using Bowden cable elements.

FIG. 4 shows the steering and braking functions of the handle 6 using Bowden cable elements. The Bowden cable elements may be used, for example, in the mobile C-arm 1, as shown in FIG. 1. FIG. 4 shows a combined brake-steering handle 6 including two Bowden cable elements 10 for braking and a Bowden cable 11 for steering. The two Bowden cable elements 10, which are fastened to the handle 6, are each controlled relative to a wheel brake element 12. Each wheel 4 is braked with the corresponding wheel brake element 12. Upon actuation of the handle 6 for the purpose of activating the braking function, tensile forces are transmitted in each case onto a wheel brake element 12 by way of the two Bowden cable elements 10. The tensile forces effect a contact pressure of the wheel brake elements 12 onto the wheels 4, and thus, the rotational movement of the wheels 4 is blocked. The control takes place using the Bowden cable 11, which is fastened to both ends of the handle 6. The Bowden cable 11 is controlled around a first gear wheel 13. The steering movement exerted by the handle 6 is conveyed to the first gear wheel 13 using the Bowden cable 11 and transmitted to a second gear wheel via a shaft 14. The first gear wheel 13 and the second gear wheel 15 are rotatably fastened to a gear wheel holding apparatus 16. Three steering gear wheels 18 are rotatably arranged on the upper side of a base plate 17. A third gear wheel 19 is rigidly fastened to each of the two wheels 4. A chain 20 is controlled around the second gear wheel 15, the third steering gear wheel 18 and around the two third gear wheels 19. The steering movement transferred onto the second gear wheel 15 is transferred onto the chain 20 and results in the two third gear wheels 19 rotating. As a result of the fixed connection of the third gear wheel 19 with the wheels 4, a rotational movement of the wheels 4 takes place.

The present embodiments are not restricted to this example. In particular, the present embodiments may also be used as C-arm devices in other mobile x-ray devices. For example, a mobile mammography device or a mobile tomosynthesis device may also be provided with one embodiment of the handle described above.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A mobile x-ray device that is operable to be moved for a change in position and operable to be controlled and braked during movement, the mobile x-ray device comprising:
    a stand; and
    a handle arranged on the stand, the handle being operable to both control and brake the mobile x-ray device,
    wherein the handle is operable to be rotated relative to the stand in a clockwise direction and a counter-clockwise direction, and
    wherein the mobile x-ray device is operable to be steered by the rotation of the handle relative to the stand and operable to be braked by a pressure on the handle, a direction of the pressure on the handle being different than the clockwise direction and the counter-clockwise direction of the rotation of the handle.

2. The mobile x-ray device as claimed in claim 1, wherein the handle is operable to be depressed or lifted relative to the mobile x-ray device to brake the mobile x-ray device.

3. The mobile x-ray device as claimed in claim 1, further comprising a display provided on the handle, wherein the display is operable to display information related to the braking.

4. The mobile x-ray device as claimed in claim 1, further comprising separate Bowden cable elements connected to the handle, wherein the mobile x-ray device is operable to be controlled and braked using the separate Bowden cable elements.

5. The mobile x-ray device as claimed in claim 1, wherein the mobile x-ray device is a C-arm.

6. The mobile x-ray device as claimed in claim 1, wherein the handle is operable to be depressed or lifted relative to the mobile x-ray device to brake the mobile x-ray device.

7. The mobile x-ray device as claimed in claim 1, further comprising a display provided on the handle, wherein the display is operable to display information related to the braking.

8. The mobile x-ray device as claimed in claim 2, further comprising a display provided on the handle, wherein the display is operable to display information related to the braking.

9. The mobile x-ray device as claimed in claim 1, further comprising separate Bowden cable elements connected to the handle, wherein the mobile x-ray device is operable to be controlled and braked using the separate Bowden cable elements.

10. The mobile x-ray device as claimed in claim 2, further comprising separate Bowden cable elements connected to the handle, wherein the mobile x-ray device is operable to be controlled and braked using the separate Bowden cable elements.

11. The mobile x-ray device as claimed in claim 3, further comprising separate Bowden cable elements connected to the handle, wherein the mobile x-ray device is operable to be controlled and braked using the separate Bowden cable elements.

12. The mobile x-ray device as claimed in claim 1, wherein the mobile x-ray device is a C-arm.

13. The mobile x-ray device as claimed in claim 2, wherein the mobile x-ray device is a C-arm.

14. The mobile x-ray device as claimed in claim 3, wherein the mobile x-ray device is a C-arm.

15. The mobile x-ray device as claimed in claim 4, wherein the mobile x-ray device is a C-arm.

* * * * *